United States Patent
Itai

(10) Patent No.: US 10,580,136 B2
(45) Date of Patent: Mar. 3, 2020

(54) MAPPING IMAGE GENERATION DEVICE, METHOD, AND PROGRAM

(71) Applicant: FUJIFILM Corporation, Tokyo (JP)

(72) Inventor: Yoshinori Itai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 199 days.

(21) Appl. No.: 15/855,279

(22) Filed: Dec. 27, 2017

(65) Prior Publication Data

US 2018/0247411 A1    Aug. 30, 2018

(30) Foreign Application Priority Data

Feb. 24, 2017   (JP) ................................ 2017-033133

(51) Int. Cl.
```
G06K 9/00      (2006.01)
G06T 7/00      (2017.01)
G06T 7/33      (2017.01)
A61B 5/055     (2006.01)
A61B 5/00      (2006.01)
```
(52) U.S. Cl.
CPC ............ *G06T 7/0014* (2013.01); *A61B 5/055* (2013.01); *A61B 5/4514* (2013.01); *A61B 5/4528* (2013.01); *G06T 7/337* (2017.01); *A61B 2576/00* (2013.01); *G06T 2200/04* (2013.01); *G06T 2207/10088* (2013.01); *G06T 2207/30008* (2013.01)

(58) Field of Classification Search
None
See application file for complete search history.

(56) References Cited

U.S. PATENT DOCUMENTS

| | | | |
|---|---|---|---|
| 2005/0065421 A1* | 3/2005 | Burckhardt | A61B 6/032 600/407 |
| 2006/0122541 A1* | 6/2006 | Tuma | A61B 5/107 600/587 |
| 2008/0128626 A1* | 6/2008 | Rousso | A61B 5/415 250/362 |
| 2014/0187908 A1 | 7/2014 | Ellermann et al. | |
| 2017/0112577 A1* | 4/2017 | Bonutti | G06T 19/006 |
| 2019/0254755 A1* | 8/2019 | Bonutti | A61B 34/20 |

FOREIGN PATENT DOCUMENTS

| | | |
|---|---|---|
| JP | 2002-532126 A | 10/2002 |
| JP | 2010-213899 A | 9/2010 |
| JP | 2016-505298 A | 2/2016 |

OTHER PUBLICATIONS

Bron, et al., "Image registration improves human knee cartilage T1 mapping with delayed gadolinium-enhanced MRI of cartilage (dGEMRIC)" Eur Radiol, 2013, vol. 23, pp. 246-252.

(Continued)

*Primary Examiner* — Atiba O Fitzpatrick
(74) *Attorney, Agent, or Firm* — Birch, Stewart, Kolasch & Birch, LLP

(57) ABSTRACT

An area extraction unit extracts a cartilage area from a morphological image. An alignment unit performs alignment between a morphological image and a functional image. A mapping unit generates a mapping image obtained by mapping the functional image to the morphological image. A display control unit displays the mapping image on a display.

11 Claims, 8 Drawing Sheets

(56) References Cited

OTHER PUBLICATIONS

Carballido-Gamio, et al., "New Techniques for Cartilage Magnetic Resonance Imaging Relaxation Time Analysis: Texture Analysis of Flattened Cartilage and Localized Intra- and Inter-subject Comparisons" Magn Reson Med., Jun. 2008, vol. 59, No. 6, pp. 1472-1477.
Nozaki, et al., "T1rho mapping of entire femoral cartilage using depth- and angle-dependent analysis" Eur Radiol, Jun. 2016, vol. 26, No. 6, pp. 1952-1962.
Office Action dated Jan. 7, 2020 in Japanese Patent Application No. 2017-033133, with English translation.

* cited by examiner

MAPPING IMAGE GENERATION DEVICE, METHOD, AND PROGRAM

CROSS REFERENCE TO RELATED APPLICATIONS

The present application claims priority under 35 U.S.C. § 119 to Japanese Patent Application No. 2017-033133 filed on Feb. 24, 2017. The above application is hereby expressly incorporated by reference, in its entirety, into the present application.

BACKGROUND

Field of the Invention

The present invention relates to a mapping image generation device, a mapping image generation device method, and a mapping image generation device program for generating a mapping image in which a functional image is mapped to a morphological image indicating a joint.

Description of the Related Art

In recent years, with the advance of medical devices such as a computed tomography (CT) device and a magnetic resonance imaging (MRI) device, a high-quality and high-resolution three-dimensional image has been used for image diagnosis. Here, since the three-dimensional image includes a large number of two-dimensional images and has a large amount of information, it may take time for a doctor to find and diagnose a desired observation part. Therefore, by recognizing an organ of interest and extracting the organ of interest from a three-dimensional image including the organ of interest using, for example, a method such as a maximum intensity projection (MIP) method and a minimum intensity projection (MinIP) method and performing an MIP display or the like, or by performing a volume rendering (VR) display of a three-dimensional image, increasing visibility of the entire organ or lesion and achieving efficiency of diagnosis have been performed.

Meanwhile, osteoarthritis is a disease that often occurs in the elderly. In particular, gonarthrosis causes pain and a reduction in a range of operation of a knee joint, and a person may not walk in a case where symptoms progress. For diagnosis of such osteoarthritis, it is necessary to qualitatively evaluate a cartilage of the knee joint. A functional image of an MRI image is known as an image for qualitatively evaluating the cartilage of the knee joint. A T2 map image which is one of functional images is an image indicating correlation with water in a tissue as a signal value. By referring to such a functional image, it is possible to perform qualitative evaluation of the cartilage of the joint.

Further, a scheme of enabling visual diagnosis of a qualitative change of a cartilage by superimposing such a functional image on an MRI image which is a morphological image indicating a form of a joint has been proposed. For example, a scheme of extracting a part separated at a predetermined distance from a bone as a distribution range of the cartilage, creating a T2 map, and mapping the T2 map to an MRI image has been proposed in order to prevent a part such as a muscle having the same T2 value as the cartilage from being extracted together with the cartilage in a case where the cartilage is extracted from the T2 map image in JP2010-213899A.

SUMMARY

Meanwhile, an image obtained by superimposing a functional image of a knee joint on a morphological image is an image of a surface of a knee joint. Here, in a case where a tissue adjacent to a cartilage is included in a functional image, a value of such a part is different from a value of the cartilage. The part having a different value from the value of the cartilage may be likely to be determined to suffer from a disease. Further, even in a case where alignment between the functional image and the morphological image is accurately performed, it is difficult for the functional image and the morphological image to be accurately associated and for an accurate state of the cartilage to be mapped to the morphological image since the functional image has a lower resolution than the morphological image.

Here, in the scheme described in JP2010-213899A, the T2 value of the cartilage based on a position in the T2 map image that is the functional image is mapped to the morphological image. However, in the scheme described in JP2010-213899A, the value of cartilage is determined on the basis of a position separated from a surface of a bone by a distance determined according to age or the like. Therefore, in a case where a thickness of a cartilage of a patient departs from a reference, it is not possible to create a T2 map that accurately indicates a state of the cartilage.

The present invention has been made in view of the above circumstances, and an object of the present invention is to enable accurately indicating a state of a cartilage in a case where a functional image is mapped to a morphological image.

A mapping image generation device according to the present invention comprises area extraction unit for extracting a cartilage area from a morphological image indicating a joint of a subject; alignment unit for aligning a functional image of the joint of the subject with the morphological image; and mapping unit for generating a mapping image obtained by mapping the functional image to the morphological image on the basis of an intermediate position in a thickness direction of the cartilage area and a result of the alignment.

The "morphological image" is an image in which a shape of the joint of the subject appears. Specifically, a T1 image, a T2 image, a T2*image, and the like acquired by an MRI can be used as morphological images.

The "functional image" is an image having a signal value according to the amount, correlation, or the like of contained substance such as water and collagen in the joint of the subject. Specifically, a T1 map, a T2 map, a T2*map, a T1ρ map, a CEST, or the like acquired by an MRI can be used as a functional image.

In the joint, one surface of the cartilage is attached to the joint and the other surface of the cartilage faces a cartilage of another joint. The "intermediate position in the thickness direction of the cartilage area" means a position between the two surfaces of the cartilage.

In the mapping image generation device according to the present invention, the mapping unit may set an intermediate surface in the thickness direction of the cartilage area as an intermediate position and map a signal value of the functional image corresponding to the intermediate surface to the morphological image to generate the mapping image.

Further, in the mapping image generation device according to the present invention, the mapping unit may set an intermediate surface in the thickness direction of the cartilage area as the intermediate position, calculate a representative value of a signal value of the functional image in a specific range in the thickness direction of the cartilage area including the intermediate surface, and map the representative value to the morphological image to generate the mapping image.

The "representative value" can be an arbitrary value as long as the value is a value representative of the signal value of the functional image. For example, an average value, an intermediate value, a maximum value, a minimum value, or the like of the signal value of the functional image can be used as the representative value.

Further, in the mapping image generation device according to the present invention, the mapping unit may divide the cartilage area into a plurality of small areas, calculate a representative value of the signal value of the functional image for each small area, and map the representative value to the morphological image to generate the mapping image.

Further, in the mapping image generation device according to the present invention, the area extraction unit extracts a bone area from the morphological image, and the mapping unit divides the cartilage area into the plurality of small areas on the basis of the bone area.

Further, in the mapping image generation device according to the present invention, the mapping unit may set an intermediate surface in the thickness direction of the cartilage area as the intermediate position, and calculate a representative value of a signal value of the functional image corresponding to the intermediate surface for each small area.

Further, in the mapping image generation device according to the present invention, the mapping unit may set an intermediate surface in the thickness direction of the cartilage area as the intermediate position, calculate a representative value of a signal value of the functional image in a specific range in the thickness direction of the cartilage area including the intermediate surface, and calculate a new representative value of the representative value for each small area.

Further, the mapping image generation device according to the present invention may further comprise a display controller for displaying the mapping image on display unit.

Further, the mapping image generation device according to the present invention may further comprise storage unit for storing a previous mapping image of the same subject as the subject, and the display controller may display a plurality of mapping images with different imaging times on the display unit.

A mapping image generation method according to the present invention comprises extracting a cartilage area from a morphological image indicating a joint of a subject; performing alignment of a functional image of the joint of the subject with the morphological image; and generating a mapping image obtained by mapping the functional image to the morphological image on the basis of an intermediate position in a thickness direction of the cartilage area and a result of the alignment.

A mapping image display method according to the present invention may be provided as a program for causing a computer to execute the mapping image display method.

Another mapping image generation device according to the present invention includes a memory that stores instructions to be executed by a computer, and a processor configured to execute the stored instructions, wherein the processor executes an area extraction process of extracting a cartilage area from a morphological image indicating a joint of a subject, an alignment process of aligning a functional image of the joint of the subject with a morphological image, and a mapping process of generating a mapping image obtained by mapping the functional image to the morphological image on the basis of an intermediate position in a thickness direction of the cartilage area and a result of the alignment.

According to the present invention, the cartilage area is extracted from the morphological image indicating the joint of the subject, the alignment of the functional image and the morphological image for the joint of the subject is performed, and the mapping image obtained by mapping the functional image to the morphological image is generated on the basis of the intermediate position in the thickness direction of the cartilage area and a result of alignment. Thus, in the present invention, since the functional image is mapped to the morphological image on the basis of the intermediate position in the thickness direction of the cartilage area, it is possible to map the signal values of the functional image reliably corresponding to the cartilage to the morphological image. Therefore, it is possible to accurately indicate the state of the cartilage in the mapping image.

DESCRIPTION OF THE PREFERRED EMBODIMENTS

Figure 1:
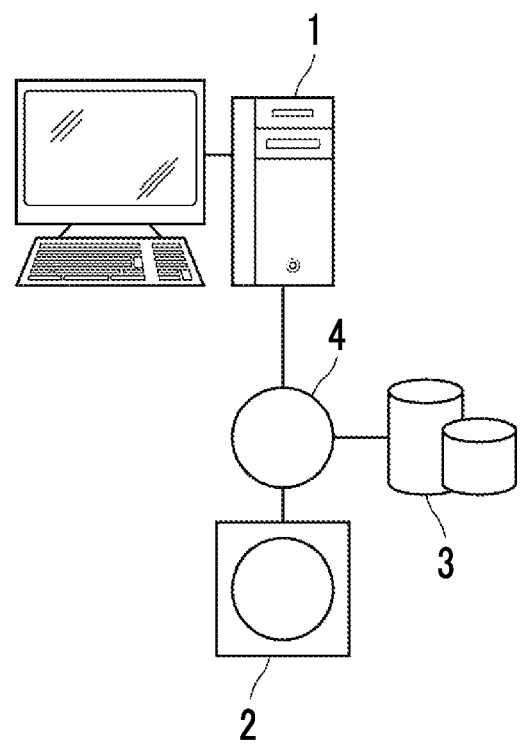
FIG. 1 is a hardware configuration diagram illustrating an overview of a diagnosis assistance system to which a mapping image generation device according to a first embodiment of the present invention is applied.

Hereinafter, embodiments of the present invention will be described with reference to the drawings. FIG. 1 is a hardware configuration diagram illustrating an overview of a diagnosis assistance system to which a mapping image generation device according to a first embodiment of the present invention is applied. As illustrated in FIG. 1, in the diagnosis assistance system, the mapping image generation device 1 according to this embodiment, a three-dimensional image capturing device 2, and an image storage server 3 are connected in a communicatable state over a network 4. In the mapping image generation device 1, a mapping image is generated from a three-dimensional image indicating a joint of a subject.

The three-dimensional image capturing device 2 is a device that generates a three-dimensional image indicating a part that is a diagnosis target of the subject by imaging the part and is, specifically, a CT device, an MRI device, and a Positron Emission Tomography (PET) device, or the like. The three-dimensional image generated by the three-dimensional image capturing device 2 is transmitted to and stored in the image storage server 3. In this embodiment, a diagnosis target part of a patient who is a subject is a knee joint, and the three-dimensional image capturing device 2 is an MRI device and generates an MRI image of the knee joint of the subject as a three-dimensional image. In particular, in this embodiment, it is assumed that a T2*image which is the morphological image G0 of the knee joint and a T2 map image which is the functional image F0 of the knee joint are generated. The T2 map image indicates correlation with water in the knee joint as a signal value. For example, the T2 map image is an image in which, as the correlation with water is higher, the signal value in each pixel increases.

Here, the morphological image G0 is generated by capturing about 300 images each having a pixel size per one image of 0.3 mm×0.3 mm. On the other hand, the functional image F0 is generated by capturing about 60 images each having a pixel size per one image of 1.5 mm×1.5 mm. Therefore, the morphological image G0 has a higher resolution than the functional image F0.

The image storage server 3 is a computer that stores and manages various pieces of data, and includes a large-capacity external storage device and database management software. The image storage server 3 performs communication with another device over a wired or wireless network 4 to transmit and receive image data or the like. Specifically, the image storage server 3 acquires various pieces of data including image data of the morphological image G0 and the functional image F0 generated by the three-dimensional image capturing device 2 over a network, and stores and manages the data in a recording medium such as a large-capacity external storage device. A storage format of the image data and communication between respective devices over the network 4 are based on a protocol such as Digital Imaging and Communication in Medicine (DICOM).

The mapping image generation device 1 is a device in which the mapping image generation program of the present invention is installed in one computer. The computer may be a workstation or a personal computer that is directly operated by a doctor who performs diagnosis, or may be a server computer that is connected to the workstation or the personal computer over a network. The mapping image generation program is recorded on a recording medium such as a digital versatile disc (DVD) or a compact disk read only memory (CD-ROM) and distributed, and installed in the computer from the recording medium. Further, the mapping image generation program is stored in an externally accessible state in a storage device of a server computer connected to the network or a network storage, and is downloaded to and installed on a computer that is used by a doctor according to a request.

Figure 2:
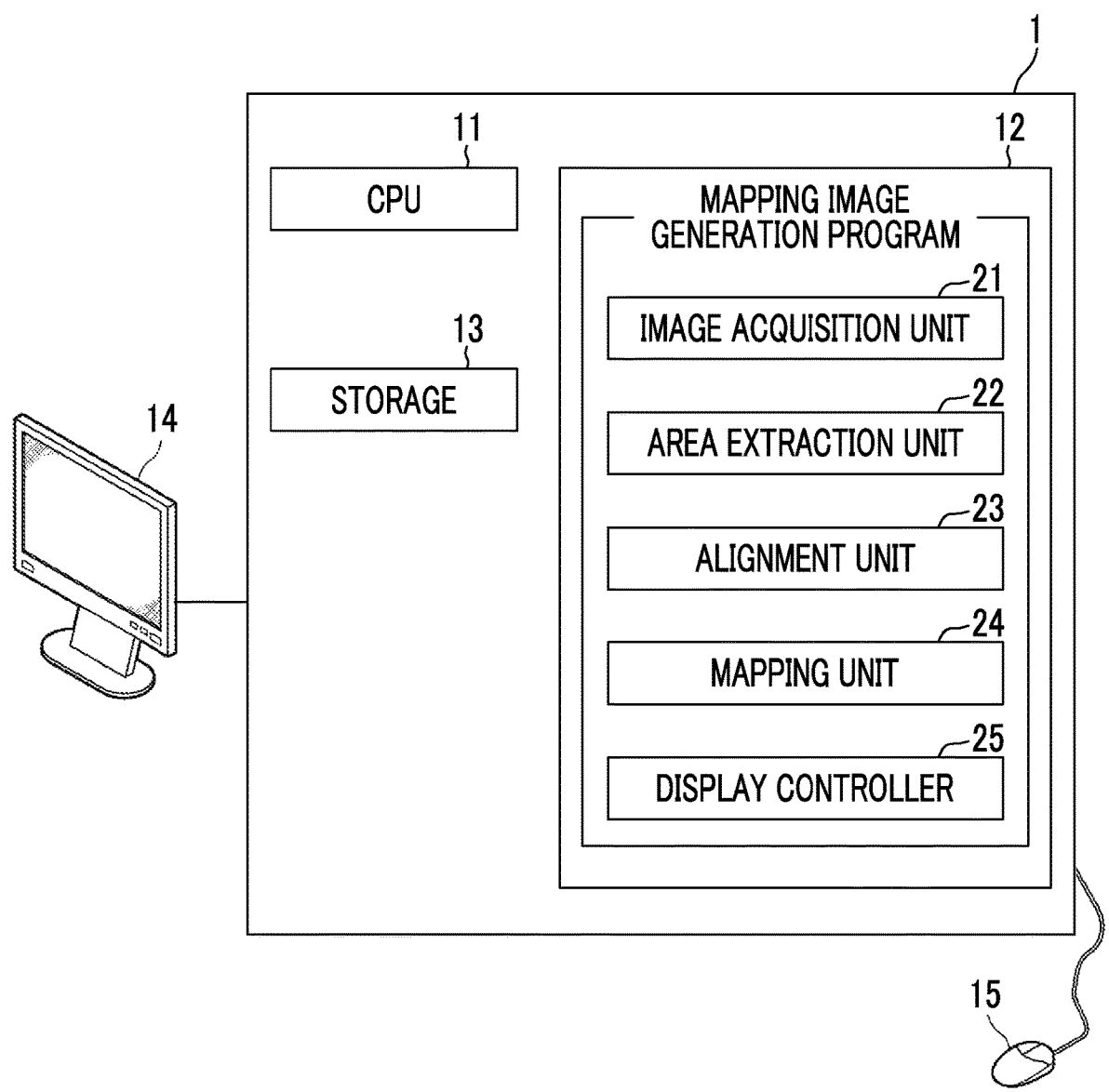
FIG. 2 is a schematic block diagram illustrating a configuration of the mapping image generation device according to the first embodiment

FIG. 2 is a diagram illustrating a schematic configuration of the mapping image generation device that is realized by installing the mapping image generation program in a computer. As illustrated in FIG. 2, the mapping image generation device 1 includes a central processing unit (CPU) 11, a memory 12, and a storage 13 as a configuration of a standard workstation. Further, a display 14, and an input unit 15 such as a mouse are connected to the mapping image generation device 1.

The storage 13 stores various types of information including a three-dimensional image of a subject acquired from the image storage server 3 over the network 4, and information necessary for a process. In this embodiment, a morphological image G0 and a functional image F0 in which a knee joint of a subject is a diagnosis target part are assumed to be stored.

Further, the mapping image generation program is stored in the memory 12. The mapping image generation program defines, as processes to be executed by the CPU 11, an image acquisition process of acquiring the morphological image G0 and the functional image F0 acquired by the three-dimensional image capturing device 2, an area extraction process of extracting a cartilage area within the knee joint from the morphological image G0, an alignment process of aligning the functional image F0 and the morphological image G0, a mapping process of generating a mapping image M0 obtained by mapping the functional image F0 to the morphological image G0 on the basis of the intermediate position in the thickness direction of the cartilage area and the alignment result, and a display control process of three-dimensionally displaying the mapping image M0 on the display 14.

The CPU 11 executes these processes according to the program such that the computer functions as the image acquisition unit 21, the area extraction unit 22, the alignment unit 23, the mapping unit 24, and the display control unit 25. The mapping image generation device 1 may include a plurality of processors or processing circuits that respectively perform the image acquisition process, the area extraction process, the alignment process, the mapping process, and the display control process. The mapping image generation device 1 of this embodiment may include only the area extraction unit 22, the alignment unit 23, the mapping unit 24, and the display control unit 25.

The image acquisition unit 21 acquires the morphological image G0 and the functional image F0 of the knee joint of the subject from the image storage server 3. In a case where the morphological image G0 and the functional image F0 have already been stored in the storage 13, the image acquisition unit 21 may acquire the morphological image G0 and the functional image F0 from the storage 13.

Figure 3:
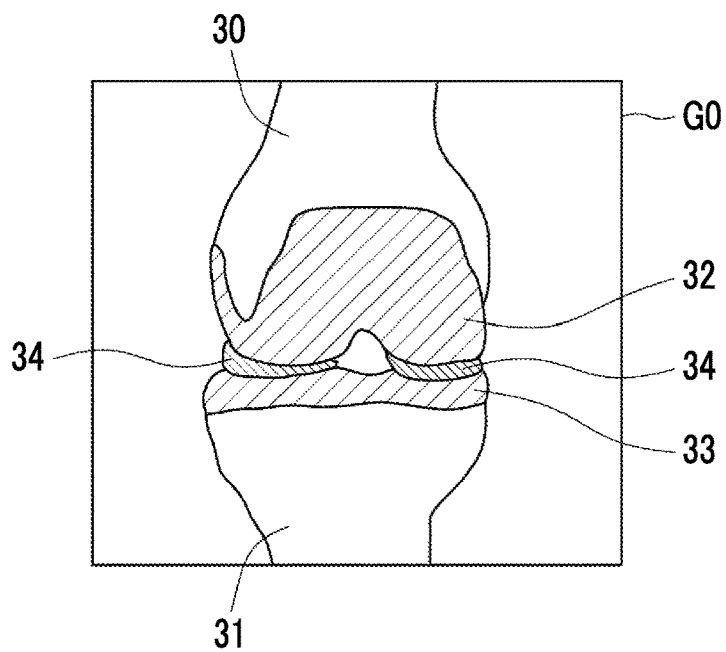
FIG. 3 is a diagram illustrating a morphological image of a knee joint.

The area extraction unit 22 extracts a cartilage area within the knee joint from the morphological image G0. In addition to the cartilage area, a bone area is also extracted. FIG. 3 is a diagram illustrating the morphological image G0 of the knee joint. As illustrated in FIG. 3, the morphological image G0 of the knee includes a femur 30 and a tibia 31. In FIG. 3, a patella is omitted for the sake of description. There is a cartilage 32 in a part facing the tibia 31 of the femur 30 and a cartilage 33 in a part facing the femur 30 of the tibia 31. Further, there is a meniscus 34 between the cartilage 32 and the cartilage 33. In this embodiment, the morphological image G0 is one type of MRI image, and a range of a pixel value (voxel value) in the morphological image G0 is different in each of bone, cartilage, meniscus, and other areas such as muscle and fat. The area extraction unit 22 extracts the bone area and the cartilage area from the morphological image G0 through threshold processing. Specifically, in the morphological image G0, an area in a range of pixel values of the bone is extracted as the bone area. Further, in the morphological image G0, an area in a range of pixel values of the cartilage is extracted as the cartilage area. The bone area includes the femur 30 and the tibia 31, and the cartilage area includes the cartilages 32 and 33.

In this embodiment, each of the cartilage 32 of the femur 30 and the cartilage 33 of the tibia 31 is extracted as the cartilage area, and a mapping image M0 for each of the cartilage areas is generated as described below. Here, generation of the mapping image M0 is performed through the same process in the femur 30 and the tibia 31. Therefore, in the following description, the generation of the mapping image M0 is performed on only the femur 30.

Here, in the morphological image G0 and the functional image F0, an included part is the same knee joint, but an imaging time is different. Therefore, the alignment unit 23 aligns the morphological image G0 and the functional image F0. As a scheme of alignment, any known method such as rigid body alignment and non-rigid alignment can be used. The alignment unit 23 may perform the alignment by deforming the functional image F0 to match the morphological image G0, or may perform the alignment by deforming the morphological image G0 to match the functional image F0. In this embodiment, it is assumed that the functional image F0 with low resolution is deformed and aligned with the morphological image G0. Accordingly, it possible to reduce the amount of calculation for the alignment, as compared with a case in which the morphological image G0 is deformed.

Figure 4:
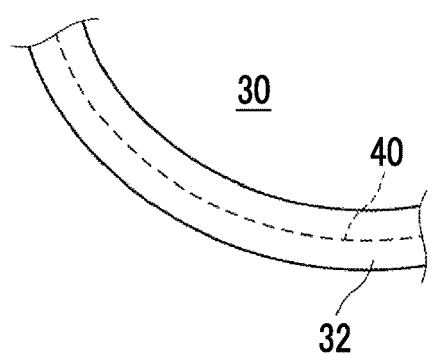
FIG. 4 is a diagram illustrating a setting of an intermediate surface in a cartilage area.

The mapping unit 24 generates the mapping image M0 by mapping the functional image F0 to the morphological image G0. Hereinafter, the generation of the mapping image M0 will be described. In this embodiment, the mapping unit 24 sets an intermediate surface in a thickness direction of the cartilage area extracted from the morphological image G0, maps a signal value of the functional image F0 corresponding to the intermediate surface to the morphological image G0 to generate the mapping image M0. FIG. 4 is a diagram illustrating the setting of the intermediate surface in the cartilage area. As illustrated in FIG. 4, the mapping unit 24 sets a surface bisecting a thickness of the cartilage 32 extracted by the area extraction unit 22 as the intermediate surface 40. The intermediate surface 40 is not limited to a surface bisecting the thickness as long as the intermediate surface is a surface between a surface of the cartilage 32 in contact with the femur bone 30 and a surface of the cartilage 32 which is an opposite surface.

Figure 5:
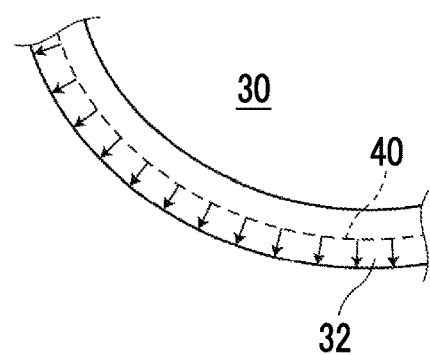
FIG. 5 is a diagram illustrating mapping.

The mapping unit 24 maps a signal value at a pixel position of the functional image F0 corresponding to each pixel position of the set intermediate surface 40 to the morphological image G0 to generate the mapping image M0. In this case, the pixel position is different between the set intermediate surface 40 and the surface of the cartilage 32. Therefore, in this embodiment, as illustrated in FIG. 5, a normal (indicated by an arrow in FIG. 5) at each pixel position on the intermediate surface 40 is set, and the signal value at the pixel position of the intermediate surface 40 at which each normal is set is mapped to a position at which each normal intersects the surface of the cartilage 32. In a case where the position at which each normal intersects with the surface of the cartilage 32 is located between the pixel positions on the surface of the cartilage 32, the signal value of the pixel position on the surface of the cartilage 32 is calculated using interpolation calculation, and the calculated signal value is mapped to the pixel position.

The display control unit 25 projects the mapping image M0 in a predetermined direction and displays the mapping image M0 on the display 14. The projection direction can be a direction in which a center line of the femur 30 extends, or a body axis direction.

Figure 6:
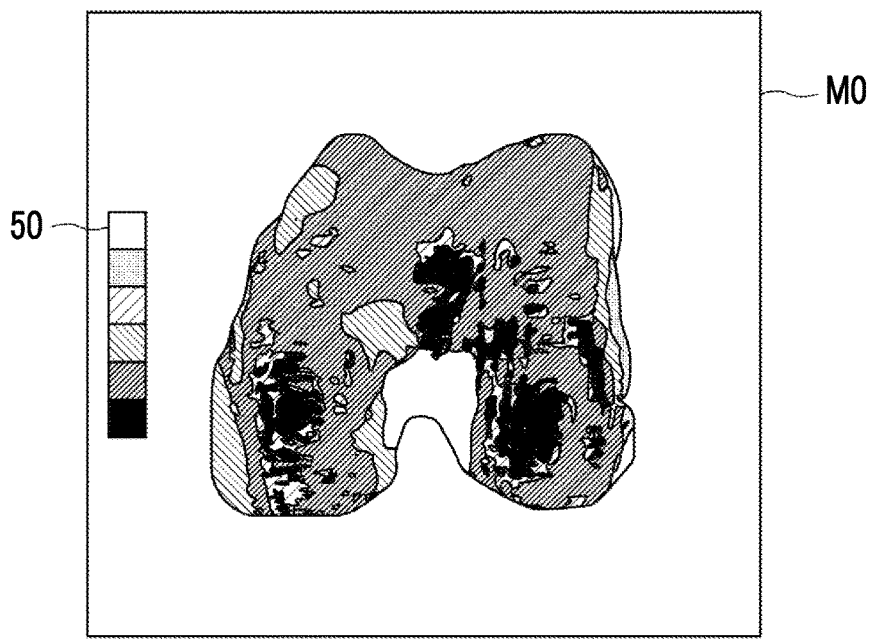
FIG. 6 is a diagram illustrating an example of a mapping image.

FIG. 6 is a diagram illustrating an example of the displayed mapping image. As illustrated in FIG. 6, in the mapping image M0, magnitude of correlation with water in the cartilage 32 of the femur 30 is indicated by six steps of color. The mapping image M0 shows that, as the color is darker, the correlation with the water is lower. In FIG. 6, a difference in color is indicated by a hatching difference. Further, the mapping image M0 includes a reference 50 indicating a relationship between color and the correlation with the water. By referring to the reference 50, it is possible to visually and easily recognize the correlation between the cartilage 32 and the water.

Figure 7:
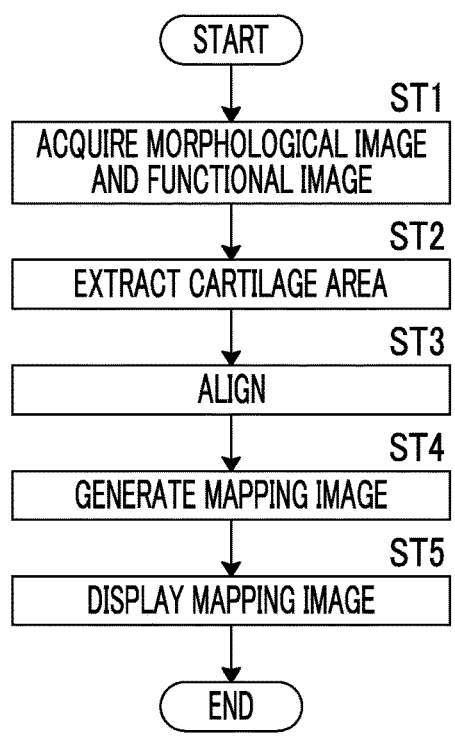
FIG. 7 is a flowchart illustrating a process that is performed in the first embodiment

Next, the process that is performed in the first embodiment will be described. FIG. 7 is a flowchart illustrating a process that is performed in the first embodiment. First, the image acquisition unit 21 acquires the morphological image G0 and the functional image F0 (step ST1), and the area extraction unit 22 extracts the cartilage area from the morphological image G0 (step ST2). Next, the alignment unit 23 aligns the morphological image G0 and the functional image F0 (step ST3). Further, the mapping unit 24 generates the mapping image M0 in which the functional image F0 is mapped to the morphological image G0 (step ST4), the display control unit 25 displays the mapping image M0 on the display 14 (step ST5), and the process is ended.

Thus, according to this embodiment, since the functional image F0 is mapped to the morphological image G0 on the basis of the intermediate position in the thickness direction of the cartilage area, the signal value of the functional image F0 reliably corresponding to the cartilage can be mapped to the morphological image G0. Therefore, it is possible to accurately indicate a state of the cartilage in the mapping image M0.

Figure 8:
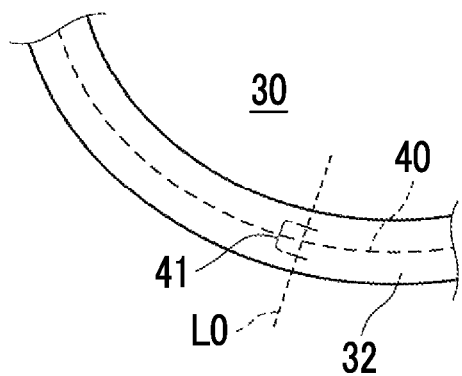
FIG. 8 is a diagram illustrating calculation of a representative value of a signal value of a functional image in a specific range in a thickness direction of a cartilage area including an intermediate surface.

Although the mapping image M0 is generated by mapping the signal value at the pixel position of the functional image F0 corresponding to each pixel position of the intermediate surface 40 set in the cartilage area to the morphological image G0 in the above embodiment, a representative value of the signal value of the functional image F0 in a specific range in the thickness direction of the cartilage area including the intermediate surface 40 may be calculated and the mapping image M0 may be generated by mapping the calculated representative value to the morphological image G0. In this case, as illustrated in FIG. 8, the mapping unit 24 sets a normal L0 at each pixel position on the intermediate surface 40 and sets a specific range 41 based on a position of the intermediate surface 40 in the normal L0. A size of the specific range 41 may be of any size as long as the specific range is between a surface of the cartilage 32 in contact with the femur bone 30 and a surface of the cartilage 32 which is an opposite surface. The mapping unit 24 calculates a representative value of the signal value of the functional image F0 in the specific range 41. As the representative value, an average value, an intermediate value, a maximum value, a minimum value, or the like can be used. The calculated representative value is mapped to the morphological image G0 to generate the mapping image M0.

Thus, it is possible to map the representative value of the signal value of the functional image F0 reliably corresponding to the cartilage to the position of the corresponding morphological image G0 by calculating the representative value of the signal value of the functional image F0 in the specific range 41 in the thickness direction of the cartilage area including the intermediate surface 40 and mapping the calculated representative value to the morphological image G0 to generate the mapping image M0.

Figure 9:
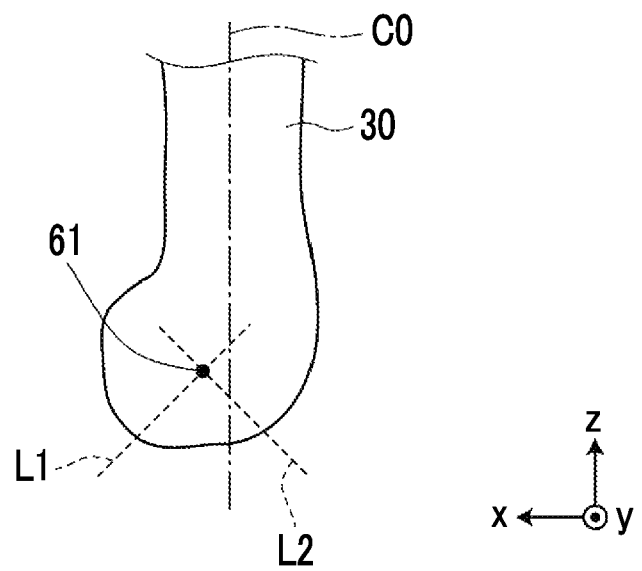
FIG. 9 is a diagram illustrating division of a cartilage area into small areas.
Figure 10:
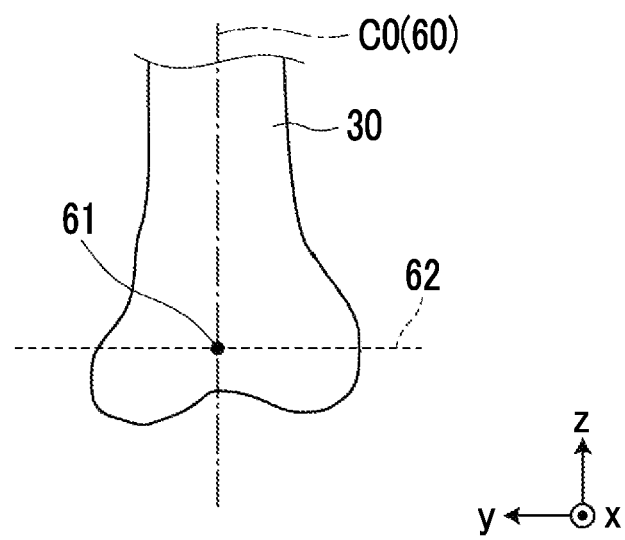
FIG. 10 is another diagram illustrating division of a cartilage area into small areas.
Figure 11:
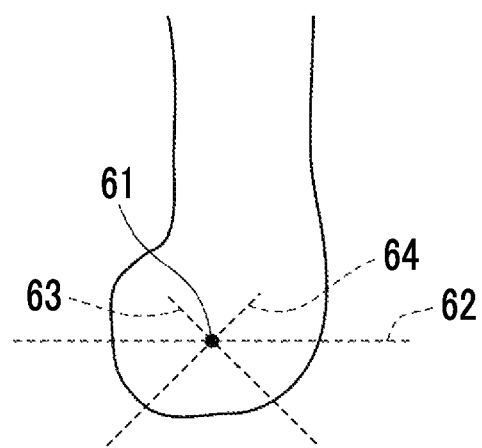
FIG. 11 is still another diagram illustrating division of a cartilage area into small areas.

Further, the cartilage area may be divided into a plurality of small areas, the representative value of the signal value of the functional image F0 may be calculated for each small area, and the calculated representative value may be mapped to the morphological image to generate the mapping image M0. FIGS. 9 to 11 are diagrams illustrating division of the cartilage area into the small areas. FIG. 9 is a diagram of the femur 30 viewed from the side of the subject. Further, here, as illustrated in FIG. 9, it is assumed that a z axis is set in a direction in which a center line C0 of the femur 30 extends, a y axis is set in a right and left direction of the subject (that is, a direction perpendicular to a paper surface), and an x axis is set in a direction orthogonal to the z axis and the y axis (that is, a right and left direction of the page). Therefore, FIG. 10 is a diagram of the femur 30 viewed from an x axis direction.

First, the mapping unit 24 sets a surface 60 passing through the center line C0 of the femur 30 and orthogonal to the y axis. The surface 60 matches the center line C0 in FIG. 10. The mapping unit 24 sets a plurality of points on a line on which the surface 60 and a joint surface of the femur 30 intersect, and obtains intersections of the normals at the points. In FIG. 9, a state in which an intersection 61 of normals L1 and L2 at two points is obtained is illustrated. As illustrated in FIG. 11, a surface 62 passing through the intersection 61 and being parallel to the y axis is set, and two surfaces 63 and 64 passing through the intersection 61 and intersecting at angles of 60° and 120° with respect to the surface 62 around a straight line extending in the y axis direction are set. The cartilage area is divided into small areas by the surfaces 60, 63, and 64.

Figure 12:
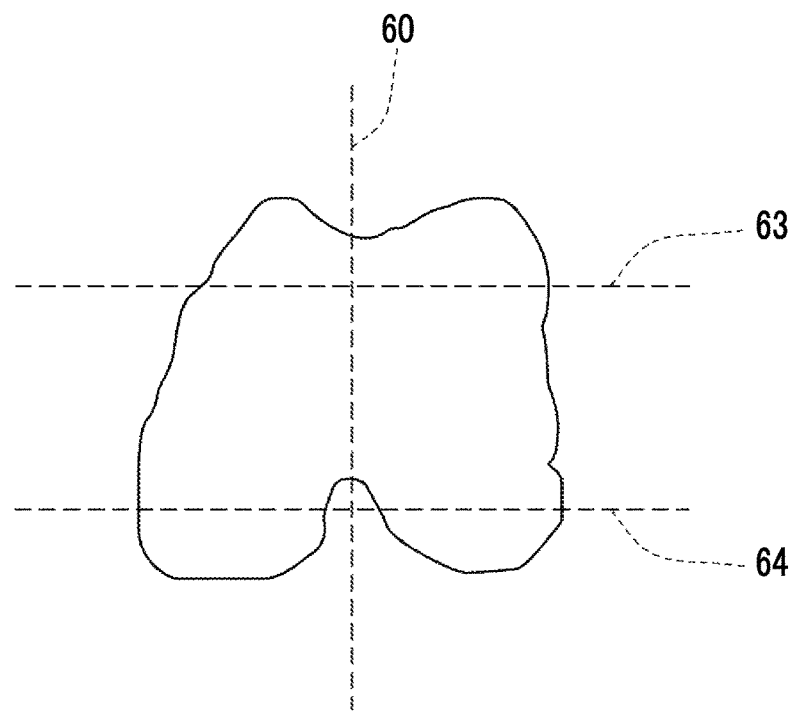
FIG. 12 is a diagram illustrating a cartilage area divided into small areas.

FIG. 12 is a diagram illustrating the cartilage area divided into small areas. FIG. 12 is a diagram obtained by projecting the morphological image G0 in a direction of the center line C0 of the femur 30. As illustrated in FIG. 12, the cartilage area is divided into six small areas by the three surfaces 60, 63, and 64.

The mapping unit 24 calculates the representative value of the signal value of the functional image F0 for each small area. The representative value may be a representative value of the signal value on the intermediate surface 40 of the functional image F0 described above. Further, the representative value of the signal value of the functional image F0 in the specific range 41 in the thickness direction of the cartilage area on the intermediate surface 40 may be calculated, and a new representative value of the representative value may be calculated.

By dividing the cartilage area into the plurality of small areas, calculating the representative value of the signal value of the functional image F0 for each small area, and mapping the representative value to the morphological image G0 to generate the mapping image M0, it is possible to confirm the state of the cartilage for each small area in the mapping image M0.

Figure 13:
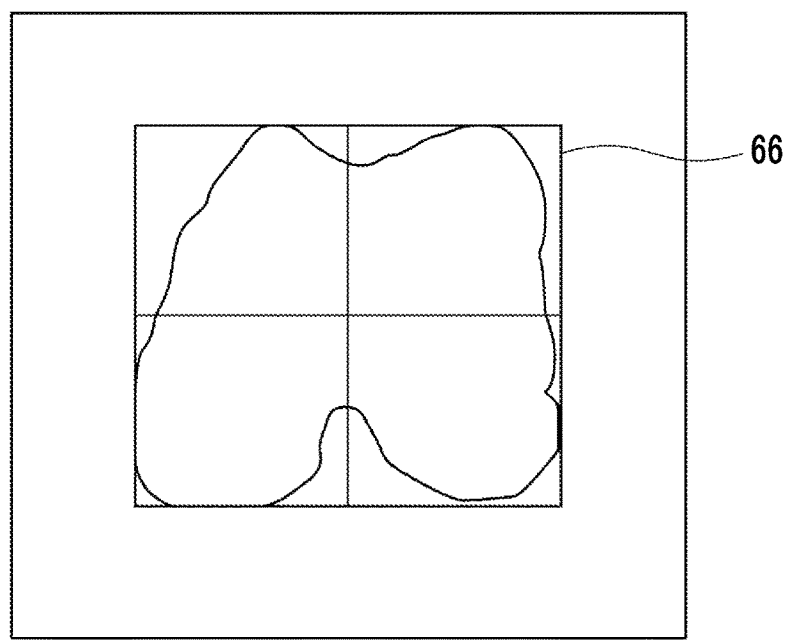
FIG. 13 is another diagram illustrating a cartilage area divided into small areas.

The division into the small areas is not limited to the above scheme, and any known scheme can be used. For example, as illustrated in FIG. 13, in a projected image obtained by projecting the morphological image G0 in the direction of the center line C0 of the femur 30, a rectangular area 66 surrounding a subchondral bone area may be set, and small areas may be set to equally divide the rectangular area into four areas.

Further, in the above embodiment, the mapping image M0 may be stored in the image storage server 3. In this case, the mapping image M0 is associated with the morphological image G0 and the functional image F0 together with, for example, information on a patient name, imaging date and time, and a method of calculating the signal value of the mapped functional image F0, and is transmitted to and stored in the image storage server 3. The mapping image M0 may also be stored in the storage 13. By storing the mapping image M0 in the image storage server 3 or the storage 13 in this manner, it is possible to perform comparative diagnosis using the mapping image M0 generated in the past for the same subject and the mapping image M0 generated from the latest morphological image G0 and the latest functional image F0. Hereinafter, this will be described as a second embodiment. A configuration of a mapping image generation device according to the second embodiment is the same as the configuration of the mapping image generation device according to the first embodiment illustrated in FIG. 2, and there is a difference in only a process to be performed. Therefore, detailed description will be omitted. The image storage server 3 or the storage 13 corresponds to storage unit.

Figure 14:
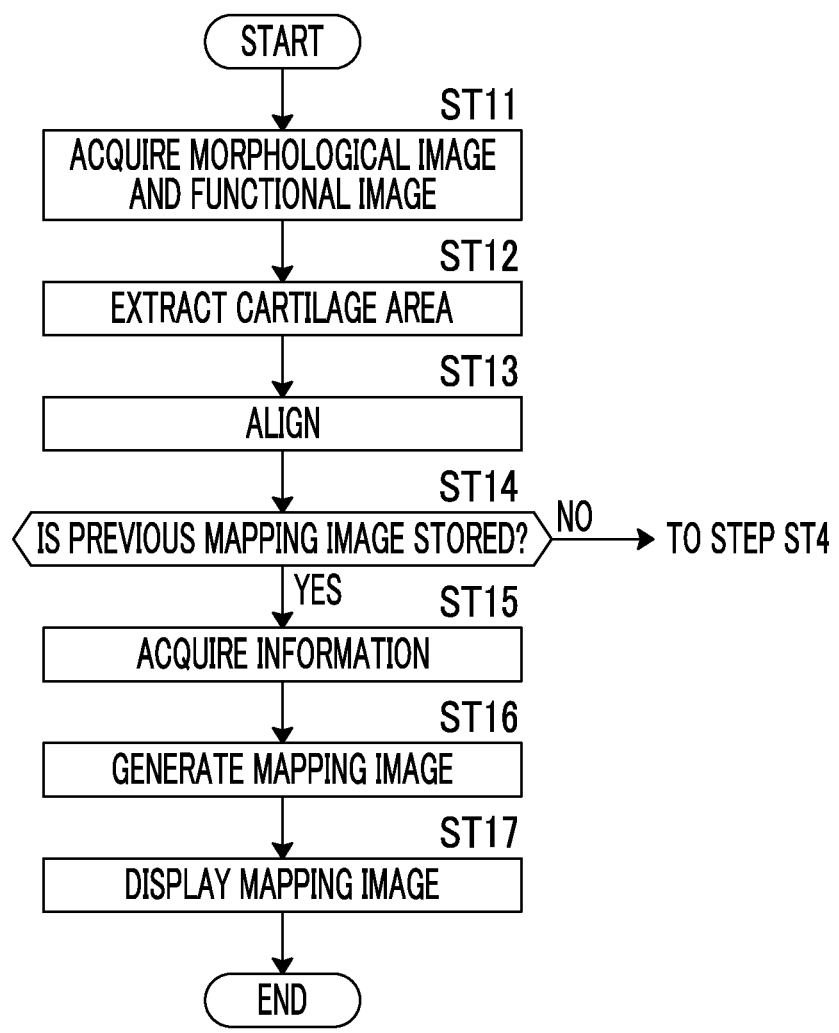
FIG. 14 is a flowchart illustrating a process that is performed in a second embodiment.

FIG. 14 is a flowchart illustrating a process that is performed in the second embodiment. First, the image acquisition unit 21 acquires the morphological image G0 and the functional image F0 (step ST11), and the area extraction unit 22 extracts the cartilage area from the morphological image G0 (step ST12). Then, the alignment unit 23 aligns the morphological image G0 and the functional image F0 (step ST13).

Then, the mapping unit 24 determines whether or not a previous mapping image M0 of the same subject is stored in the image storage server 3 or the storage 13, together with the information on the method of calculating the signal value of the functional image F0 with respect to the morphological image G0 and the functional image F0 of the process target (step ST14).

In a case where a result in step ST14 is positive, the mapping unit 24 acquires, from the image storage server 3 or the storage 13, the information on the method of calculating the signal value of the functional image F0 stored together with the previous mapping image M0 of the same subject (information acquisition: step ST15). Then, on the basis of the acquired information, the mapping unit 24 calculates the signal value of the functional image F0 mapped to the morphological image G0 using the same scheme as in a case where the previous mapping image M0 is generated, and generates the mapping image M0 (step ST16). The display control unit 25 displays the generated mapping image M0 and the previous mapping image M0 on the display 14 (step ST17), and the process is ended.

On the other hand, in a case where the result in step ST14 is negative, the process proceeds to step ST4 of the first embodiment, in which the generation of the mapping image M0 and the display on the display 14 are performed, and the process is ended.

Thus, in the second embodiment, since the previous mapping images M0 for the same subject are stored in the image storage server 3 or the storage 13 and a plurality of mapping images M0 with different imaging times are displayed on the display 14, it is possible to confirm a change in the state of the cartilage over time. In particular, by calculating the signal value of the functional image F0 mapped to the morphological image G0 using the same scheme as in a case where the previous mapping image M0 is generated and generating the mapping image M0, it is possible to confirm a change in the cartilage over time more accurately.

In the above embodiment, the mapping image of the knee joint is generated, but the present invention is not limited thereto, and it is understood that the present invention can be applied even in a case where a mapping image of an elbow joint, a hip joint, a shoulder joint, a facet joint, or the like is generated.

Further, in the above embodiment, the T2*image is used as the morphological image G0 and the T2 map image is used as the functional image F0, but the present invention is not limited thereto, and a T1 image, a T2 image, or the like may be used as the morphological image G0. Further, a T1 map image, a T2*map image, a T1ρ map image, a CEST, or the like can be used as the functional image F0.

Hereinafter, an operation and effects of this embodiment will be described.

By setting the intermediate surface in the thickness direction of the cartilage area as the intermediate position and mapping the signal values of the functional image corresponding to the intermediate surface to the morphological image to generate the mapping image, it is possible to map the signal values of the functional image reliably corresponding to the cartilage to the morphological image. Therefore, in the mapping image, it is possible to indicate the state of the cartilage more accurately.

By setting the intermediate surface in the thickness direction of the cartilage area as the intermediate position, calculating the representative value of a signal value of the functional image in a specific range in the thickness direction of the cartilage area including the intermediate surface, and mapping the representative value to the morphological image to generate the mapping image, it is possible to map the representative value of the signal value of the functional image reliably corresponding to the cartilage to the position of the corresponding morphological image.

By dividing the cartilage area into a plurality of small areas, calculating the representative value of the signal value of the functional image for each small area, and mapping the representative value to the morphological image to generate the mapping image, it is possible to confirm the state of the cartilage in each small area.

By storing the previous mapping image of the same subject as the subject and displaying the plurality of mapping images with different imaging times on the display unit, it is possible to confirm a change in the state of the cartilage over time.

What is claimed is:

1. A mapping image generation device comprising:
    processing circuitry configured to:
        extract a cartilage area from a morphological image indicating a joint of a subject;
        align a functional image of the joint of the subject with the morphological image; and
        generate a mapping image obtained by mapping the functional image to the morphological image on the basis of an intermediate position in a thickness direction of the cartilage area and a result of the alignment.

2. The mapping image generation device according to claim 1, wherein the processing circuitry is further configured to set an intermediate surface in the thickness direction of the cartilage area as an intermediate position and map a signal value of the functional image corresponding to the intermediate surface to the morphological image to generate the mapping image.

3. The mapping image generation device according to claim 1, wherein processing circuitry is further configured to set an intermediate surface in the thickness direction of the cartilage area as the intermediate position, calculate a representative value of a signal value of the functional image in a specific range in the thickness direction of the cartilage area including the intermediate surface, and map the representative value to the morphological image to generate the mapping image.

4. The mapping image generation device according to claim 1, wherein processing circuitry is further configured to divide the cartilage area into a plurality of small areas, calculate a representative value of the signal value of the functional image for each small area, and map the representative value to the morphological image to generate the mapping image.

5. The mapping image generation device according to claim 4,
    wherein the processing circuitry is further configured to:
        extract a bone area from the morphological image, and
        divide the cartilage area into the plurality of small areas on the basis of the bone area.

6. The mapping image generation device according to claim 4, wherein the processing circuitry is further configured to set an intermediate surface in the thickness direction of the cartilage area as the intermediate position, and calculate a representative value of a signal value of the functional image corresponding to the intermediate surface for each small area.

7. The mapping image generation device according to claim 4, wherein the processing circuitry is further configured to set an intermediate surface in the thickness direction of the cartilage area as the intermediate position, calculate a representative value of a signal value of the functional image in a specific range in the thickness direction of the cartilage area including the intermediate surface, and calculate a new representative value of the representative value for each small area.

8. The mapping image generation device according to claim 1, wherein the processing circuitry is further configured to display the mapping image on display.

9. The mapping image generation device according to claim 8, further comprising:
    storage for storing a previous mapping image of the same subject as the subject,
    wherein the processing circuitry is further configured to display a plurality of mapping images with different imaging times on the display.

10. A mapping image generation method comprising:
    extracting a cartilage area from a morphological image indicating a joint of a subject;
    performing alignment of a functional image of the joint of the subject with the morphological image; and
    generating a mapping image obtained by mapping the functional image to the morphological image on the basis of an intermediate position in a thickness direction of the cartilage area and a result of the alignment.

11. A non-transitory computer-readable recording medium having stored therein a mapping image generation program that causes a computer to execute:
    a process of extracting a cartilage area from a morphological image indicating a joint of a subject;
    a process of performing alignment of a functional image of the joint of the subject with the morphological image; and
    a process of generating a mapping image obtained by mapping the functional image to the morphological image on the basis of an intermediate position in a thickness direction of the cartilage area and a result of the alignment.

* * * * *